United States Patent
Haketa et al.

(10) Patent No.: US 8,017,404 B2
(45) Date of Patent: Sep. 13, 2011

(54) STEROID HORMONE ASSAY METHOD

(75) Inventors: Noriko Haketa, Tokyo (JP); Shingo Kakuo, Haga-gun (JP); Seijiro Honma, Yokohama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/676,226

(22) PCT Filed: Sep. 8, 2008

(86) PCT No.: PCT/JP2008/066187
§ 371 (c)(1),
(2), (4) Date: Mar. 3, 2010

(87) PCT Pub. No.: WO2009/034951
PCT Pub. Date: Mar. 19, 2009

(65) Prior Publication Data
US 2010/0184095 A1 Jul. 22, 2010

(30) Foreign Application Priority Data
Sep. 12, 2007 (JP) ................. 2007-236250

(51) Int. Cl.
G01N 33/53 (2006.01)
G01N 33/00 (2006.01)

(52) U.S. Cl. ......... 436/127; 435/7.21; 435/7.2; 435/7.1; 435/4

(58) Field of Classification Search .................. 436/127; 435/7.21, 7.2, 7.1, 4
See application file for complete search history.

(56) References Cited

U.S. PATENT DOCUMENTS

2005/0244908 A1* 11/2005 Horsewood et al. ............ 435/11
2005/0272112 A1* 12/2005 Horsewood et al. ............ 435/11

FOREIGN PATENT DOCUMENTS

| JP | 2006-138786 | * | 6/2006 |
| JP | 2006-138786 | A | 6/2006 |
| JP | 2007-108060 | A | 4/2007 |
| WO | WO 03/103685 | A1 | 12/2003 |

OTHER PUBLICATIONS

International Search Report for PCT/JP2008/066187, mailed Dec. 9, 2008 from the Japanese Patent Office.
Griffiths, WJ, et al., "Derivatisation for the characterisation of neutral oxosteroids by electrospray and matrix-assisted laser desorption/ionisation tandem mass spectrometry: the Girard P derivative," Rapid Commun Mass Spectrom 17(9): 924-935, Wiley Interscience, Malden, MA (Jan. 2003).
Imaeda, K. et al., "Effect of sex-hormone on components of rat skin surface lipid," Nippon Yakurigaku Zasshi [Folia Pharmacologica Japonica], 90(3): 147-153, The Japanese Pharmacological Society, Tokyo, Japan (Sep. 1987) (English translation with Japanese language document attached).
Khan, MA, et al., "Analysis of derivatised steroids by matrix-assisted laser desorption/ionisation and post-source decay mass spectrometry," Steroids, 71(1): 42-53, Elsevier, Amsterdam, The Netherlands (Jan. 2006).
Pershing LK, et al., "Feasibility of measuring the bioavailability of topical betamethasone dipropionate in commercial formulations using drug content in skin and a skin blanching bioassay," Pharm Res 9(1):45-51, Plenum Press, New York, NY (Jan. 1992).
esp@cenet English abstract for JP2007-108060(A), published Apr. 26, 2007.
esp@cenet English abstract for JP2006-138786(A), published Jun. 1, 2006.
International Preliminary Report on Patentability (Chapter I) for PCT/JP2008/066187, mailed Mar. 30, 2010 from the International Bureau of WIPO, Geneva Switzerland.
Extended European Search report for EP Appl. No. 08830449.8, mailed Sep. 13, 2010, from the European Patent Office, Munich, Germany.
Ikeda, Y., et al., "In vivo assessment of the cutaneous bioavailability of topically applied maxacalcitol," Methods Find Exp Clin Pharmacol: 27(5): 305-310 (Jun. 2005), Prous, Barcelona.
Hayashi, M., et al., "Comparison of the effects of calcitriol and maxacalcitol on secondary hyperparathyroidism in patients on chronic haemodialysis: a randomized prospective multicentre trial," Nephrol Dial Transplant 19: 2067-2073 (Aug. 2004), Oxford University Press, England.
Zouboulis, CC., et al., "Sexual hormones in human skin," Horm Metab Res 39(2): 85-95 (Feb. 2007), Thieme, Germany.
Khan, MA et al., "Analysis of derivatised steroids by matrix-assisted laser desorption/ionisation and post-source decay mass spectrometry," Steroids 71(1): 42-53 (Jan. 2006), Elsevier, United States.
Griffiths, WJ, et al., "Derivatisation for the characterisation of neutral oxosteroids by electrospray and matrix-assisted laser desorption/ionisation tandem mass spectrometry: the Girard P derivative," Rapid Commun Mass Spectrom 17(9): 924-935 (Jan. 2003), John Wiley and Sons Ltd, England.
Reel, JR et al., "Survey and Assessment of Mammalian Estrogen Biological Assays for Hazard Characterization" Fundam. Appl. Toxicol. (now Tox. Sci.) 34: 288-305 (Dec. 1996), Academic Press, United States.

* cited by examiner

*Primary Examiner* — Christine T Mui
(74) *Attorney, Agent, or Firm* — Sterne, Kessler, Goldstein & Fox P.L.L.C.

(57) ABSTRACT

The level of a steroid hormone, including estrogen, in the stratum corneum of the skin is assayed by LC-MS analysis of a steroid hormone in the stratum corneum of the skin collected by a tape stripping method. This allows the concentration in the skin of the steroid hormone, including estrogen which has an important effect on the state of the skin, to be easily measured.

7 Claims, No Drawings

STEROID HORMONE ASSAY METHOD

TECHNICAL FIELD

The present invention relates to a method for assaying the level of a steroid hormone present in the stratum corneum of the skin.

BACKGROUND ART

Estrogen is a type of sex hormone classified as a steroid hormone, and is called an estrogenic hormone or a female hormone. Estrogen is produced in the ovaries, transported around the body, and binds to estrogen receptors in the cytoplasm. The estrogen-bound receptor translocates into the nucleus, and exhibits strong, wide-ranging physiological effects even in minute amounts. For example, regarding the skin, estrogen has important effects including: (a) promoting blood flow; (b) improving the skin's ability to retain moisture by increasing mucopolysaccharides such as hyaluronic acid and the like; and (c) conferring elasticity to the skin by increasing elastin and collagen.

Therefore, attempts have been made to obtain an idea of the concentration of estrogen in the body. For example, there is a method in which estrogen from a tissue-derived sample obtained from serum, saliva, urine, cultured cells, or the organs is extracted with a solvent. The obtained extract is reacted with a pentahalogenated benzyl compound or a pentahalogenated benzoyl compound, and the resultant product is further reacted with 1-lower alkyl-2-halogenated pyridine. The obtained reaction mixture is then measured by LC-MS (Patent Document 1).

On the other hand, the stratum corneum is the outermost layer of the skin, and covers the cuticles. The stratum corneum has a barrier function against the intrusion of bacteria and viruses, a moisture retaining function for preventing the loss of moisture and moisturizing ingredients in the skin, and a protection function for mitigating external stimuli and the like. However, the stratum corneum is formed from "dead cells" that have lost their cell nucleus during the cornification of the skin cells. Therefore, the estrogen concentration in the stratum corneum is not measured. Rather, the estrogen concentration in the skin is measured by collecting skin tissue or blood.

Furthermore, similarly for progesterone and testosterone, which among steroid hormones are classified as sex hormones, measurement of the concentration of progesterone and testosterone in the body is usually carried out from collection of serum, saliva, urine and the like. Currently, there are no examples of measuring based on the stratum corneum.
[Patent Document 1] JP-A-2006-138786

DISCLOSURE OF THE INVENTION

Problems to be Solved by the Invention

In view of the above, it is an object of the present invention to enable the concentration in the skin of a steroid hormone, including estrogen which has an important effect on the state of the skin, to be easily measured.

Means for Solving the Problems

The present inventors have discovered that, surprisingly, the steroid hormone such as estrogen which enters into the cell nucleus and exhibits various physiological effects is present in the stratum corneum, which is formed from "dead cells" that lack a cell nucleus. The present inventors have also discovered that the level of the steroid hormone in a stratum corneum can be measured very easily by collecting the stratum corneum by a tape stripping method and analyzing the level of the steroid hormone in the stratum corneum.

More specifically, the present invention provides a method for assaying a level of a steroid hormone in a skin stratum corneum by quantitative analysis by LC-MS of the steroid hormone in a skin stratum corneum collected by a tape stripping method.

Advantages of the Invention

According to the present invention, a stratum corneum of the skin is collected by tape stripping of the stratum corneum of the skin, and the concentration of a steroid hormone such as estrogen in the stratum corneum of the skin is assayed. Therefore, there is little burden on a test subject.

Furthermore, since the stratum corneum of the skin, which is the outermost layer of the skin, strikingly reflects the state of the inner layers of the skin, knowing the level of a steroid hormone in the stratum corneum of the skin is useful in analyzing the state of the whole skin including the skin inner layers.

BEST MODE FOR CARRYING OUT THE INVENTION

The present invention is a method for assaying by LC-MS a level of a steroid hormone such as estrogen based on a stratum corneum of the skin collected by a tape stripping method.

Here, the term "steroid hormone" refers to a hormone having a steroid skeleton. Steroid hormones are especially suited to assaying the level of the female hormones estrogen and progesterone and the male hormone testosterone. Further, the term "estrogen" refers to estradiol and estradiol derivatives.

Tape stripping is a method in which a strip of tape having an adhesive agent layer on a surface is stuck onto a test site and then peeled off so that the surface of the test site is allowed to adhere to the adhesive surface of the tape for collection.

In the present invention, the tape for performing the tape stripping method may be any tape as long as it can be closely adhered to the skin and then peeled off. Examples of such a tape include commercially-available adhesive tapes. More specifically, the adhesive agent layer of such tape may be formed from a rubber, acrylic, silicon or other such adhesive agent. The tape body for supporting the adhesive agent layer may be formed from paper or cloth composed of natural or synthetic fibers, or from a plastic sheet composed of polyester, polyimide, polyphenylene sulfide, polypropylene and the like. Among these, from the perspectives of solvent resistance and background (steroid hormone level detected from the tape), polyphenylene sulfide (PPS) is preferred.

On the other hand, the site on the body where the stratum corneum of the skin is collected by the tape stripping method is not especially limited, and may be a place where the state of the skin is cosmetically important, such as the face, neck, arms or the like.

The tape on which the stratum corneum of the skin is adhered which is used in the tape stripping method is, either cut or in its original form, dipped in a solvent such as ethyl alcohol, hexane, acetone, ethyl acetate and the like, to extract the steroid hormone. Then, the resultant extract solution is purified. The method for purifying the extract solution is preferably carried out by column separation to separate and remove impurities from the steroid hormone.

To improve the detection sensitivity during the subsequent assay by LC-MS, it is preferred to appropriately introduce a substituent into the steroid hormone in the purified extract solution to form a derivative of the steroid hormone.

For example, as described in JP-A-2006-138786 (Patent Document 1), to improve the detection sensitivity of estradiol, a pentahalogenated benzyl group or a pentahalogenated benzoyl group is introduced into estrogen by reacting a pentahalogenated benzyl compound or a pentahalogenated benzoyl compound with estrogen, and the resultant product is reacted with 1-lower alkyl-2-halogenated pyridine to introduce 1-lower alkyl pyridinium into the estrogen.

In this case, for estradiol it is preferred to perform the reaction with the 1-lower alkyl-2-halogenated pyridine after the reaction with the pentahalogenated benzyl compound or the pentahalogenated benzoyl compound, because the detection sensitivity by LC-MS can be heightened by selectively reacting the pentahalogenated benzyl compound or the pentahalogenated benzoyl compound with a phenolic hydroxyl group of the estradiol.

Furthermore, to improve the detection sensitivity of progesterone, the O-ethylhydroxylammonium chloride, a Girard's reagent T, or a Girard's reagent P as a ketone-deriving reagent is reacted with the carbonyls at position 3 and 20 of the progesterone to form an imino derivative.

Moreover, to improve the detection sensitivity of testosterone, an acyl derivative is formed using an acylating reagent, although it is preferred to form a picolinoyl derivative. Alternatively, a pyridinium derivative is formed using 2-fluoro-1-methyl pyridine.

After thus appropriately forming a derivative of the steroid hormone, the steroid hormone derivative is detected by LC-MS, and the level of the steroid hormone is assayed.

Here, as the LC-MS, LC-MS/MS, LC-ESI-MS/MS, LC-APCI-MS/MS and the like may be employed. These measurements themselves can be carried out based on a typical method.

Furthermore, based on the level of the thus-obtained steroid hormone in the stratum corneum of the skin, the level of the steroid hormone in the skin inner layers can be estimated. Therefore, the level of the steroid hormone measured according to the present invention is useful in researching the relationship between the state of the skin and the level of a steroid hormone, and in researching the impact of cosmetics and beauty treatments on the level of a steroid hormone.

EXAMPLES

The present invention will now be described in more detail based on the following examples.

Example 1

(1) Collection of the Stratum Corneum of the Skin

Five strips of 6 cm×2.5 cm PPS tape (Nichiban Co., Ltd.) as tape to be used for tape stripping were stuck on the cheek region of 4 test subjects (females in their twenties) A, B, C, and D. The tape was then peeled off to collect the stratum corneum of the skin of each test subject.

(2) Sample Purification

A 1 cm-wide piece around the center of each strip of tape on which the stratum corneum of the skin was collected was cut out and removed with scissors for a protein assay. The rest of each strip of tape was dipped in an ethanol solution and purified as follows to produce a sample for an estradiol assay.

Specifically, 25 mL of ethanol and estradiol-$^{13}C_4$ (100 pg) as a surrogate substance for determining the recovery ratio in the purification operation were added onto each strip of tape from which the 1 cm-wide piece around the center had been cut out and removed. The strips of tape were shaken for 3 hours at 50° C., then vigorously shaken for a further 10 minutes with an extractor, and then the ethanol was collected. Next, 10 mL of purified water and 10 mL of ethanol were charged into the container containing the tape, and the container was vigorously shaken for a further 10 minutes with the extractor. The aqueous ethanol solution was collected and added to the previously-collected ethanol. The ethanol was concentrated with a 40° C. centrifugal evaporator and the resultant concentrated solution was adjusted to 4 mL solution by the addition of ethanol. The ethanol solution was charged with 0.5 mL of purified water and stirred. The resultant mixture was then left to stand for 5 hours or more at 5 to 15° C. (when at −20 to −10° C., it is left to stand for about 2 hours), and separated by centrifugation. The supernatant was charged with 3 mL of hexane, and the resultant mixture was stirred and separated by centrifugation. The supernatant was then discarded. The ethanol layer was removed by distillation using the centrifugal evaporator. The resultant product was dissolved in 250 μL of methanol and diluted with 1.25 mL of purified water to obtain a sample.

(3) Estradiol Assay (3-1) Preparation of Estradiol-3-pentafluorobenzyl Ether

The sample purified in (2) was added to granular acidic silica (Shimadzu GLC Ltd., Bond Elut C18), and then successively washed with 2 mL of purified water and 1.5 mL of a 30% acetonitrile aqueous solution. The estradiol-testosterone fraction was eluted with 2.5 mL of a 40% acetonitrile aqueous solution, the progesterone was eluted with a 70% acetonitrile aqueous solution, and each eluate was removed by distillation.

The obtained estradiol-testosterone fraction was separated into estradiol and testosterone by HPLC to obtain an estradiol extract.

Next, this estradiol extract was dissolved in 50 μL of acetonitrile. The resultant solution was charged with 50 μL of a 0.8% potassium hydroxide/ethanol solution and 50 μL of a 5% pentafluorobenzyl bromide/acetonitrile solution. The resultant mixture was left for 60 minutes in a temperature-controlled reaction vessel at 54 to 57° C. to react the estradiol and the pentafluorobenzyl bromide.

The solvent in this reaction solution was removed by distillation under nitrogen gas. The resultant product was charged with 0.75 mL of purified water and 4 mL of an ether solution, and the resultant mixture was shaken for 10 minutes. Next, the reaction product of the estradiol and the pentafluorobenzyl bromide was extracted in ether. Then, a purified product of estradiol-3-pentafluorobenzyl ether was obtained by separating the ether solution by a freeze method and removing the ether by distillation under nitrogen gas.

(3-2) Preparation of Estradiol-3-Pentafluorobenzyl Ether 17-O-Methyl Pyridinium

The estradiol-3-pentafluorobenzyl ether prepared in (3-1) was dried for 1 hour under reduced pressure, and the resultant product was charged with 200 μL of a 2% 2-fluoro-1-methyl pyridinium p-toluene sulfonate/dichloromethane solution and 30 μL of a 10% triethylamine/dichloromethane solution. The resultant mixture was left for 1.5 hours at room temperature. The solvent in this reaction solution was removed by distillation under nitrogen gas. The resultant product was then dissolved in 250 μL of methanol, and diluted with 1 mL of purified water to obtain an estradiol-3-pentafluorobenzyl ether 17-O-methyl pyridinium solution.

(3-3) Estradiol-3-Pentafluorobenzyl Ether 17-O-Methyl Pyridinium Assay

The estradiol-3-pentafluorobenzyl ether 17-O-methyl pyridinium solution prepared in (3-2) was added onto granular acidic silica (Shimadzu GLC Ltd., Bond Elut C18), and then successively washed with 1 mL of purified water, 5 mL of a 0.3% ammonia aqueous solution, 3 mL of methanol, and 3 mL of a 0.01% formic acid aqueous solution/methanol (1:1). Then, the estradiol fraction was eluted with 4 mL of a mixed solution of acetonitrile/a 10% formic acid aqueous solution (4:1), and the solvent of the eluate was removed by distillation with the centrifugal evaporator. The reaction sample was then dissolved in 0.1 mL of a mixed solution of acetonitrile/a 0.05% formic acid aqueous solution (3:1) to obtain an LC-MS/MS measurement sample.

The LC-MS/MS measurement was carried out under the following conditions.

1) LC Part
Column: Xterra 3 μm 2.1×100 mm
Column temperature: 40° C.
Mobile phase and flow rate: Mixed solution of acetonitrile/a 0.05% formic acid aqueous solution (3:1) at 0.2 mL/min
Charged amount: 20 mL
2) MS Part
MS: API-5000 (Applied Biosystems)
Ionization method: Positive ions ESI
Capillary voltage: 3.5 kV
Cone voltage: 35, 40 V
Collision energy: 18 eV
Ion source temperature: 120° C.
Measurement ion: 544.4 339, 110.1 (Estradiol), 547.4→339 (I.S)

Further MS measurement of the m/z=544.4 peak detected in this MS measurement obtained a peak at m/z=339, 110.1. When this was subjected to SRM (selected reaction monitoring) chromatogram measurement, estradiol was detected.

Further, in this estradiol assay, a calibration curve was used in which estradiol labeled with deuterium was used as the internal standard.

(4) Progesterone Assay

Using the 70% acetonitrile eluate of (3-1), the progesterone assay was carried out in the same manner as in (3-3) using LC-MS/MS.

(5) Testosterone Assay

Using the testosterone solution separated from the estradiol-testosterone fraction in (3-1), the testosterone assay was carried out in the same manner as in (3-3) using LC-MS/MS.

(6) Conversion of the Estradiol, Progesterone, and Testosterone Levels in the Stratum Corneum (6-1) Preparation Method of Samples for Protein Assay The 1 cm piece from the center portion which was cut out and removed from the tape on which the stratum corneum of the skin was collected in (2) was dipped in a buffer (0.1 N NaOH), 1% SDS). Extraction was carried out for 2 hours in an oven set to 70° C. to obtain a sample for the protein assay.

(6-2) Protein Assay

The protein assay was carried out in the following manner using a BCA protein assay kit (Pierce, manufactured by Techno Chemical Corp.).

(i) Reagent A and Reagent B were mixed in a 50:1 ratio.

(ii) 200 μL of (i) was dispensed into each well in a 96-well plate.

(iii) The dispensed solution was charged with 20 μL of a protein standard solution (2 mg, 1.5 mg, 1 mg, 0.75 mg, 0.5 mg, 0.25 mg, 0.125 mg, 0.025 mg, and 0 mg/mL BSA solution) or 20 μL the sample, and the resultant mixture was incubated for 30 minutes at 37° C.

(iv) Absorbance at 575 nm was measured using a plate reader (BIO-RAD Model 550) to assay the protein concentration.

(6-3) Conversion of the Estradiol, Progesterone, and Testosterone Levels in the Stratum Corneum The levels of estradiol, progesterone, and testosterone obtained in (3) to (5) were converted by the protein level in the collected sample to calculate the level of steroid hormone per 1 mg of protein in the stratum corneum.

The results are shown in Table 1.

Reference Example 1

Measurement of Steroid Hormone in Saliva

The estradiol-$^{13}$C4 (100 pg) of an internal standard product was added to saliva (1 to 2 mL) and extraction was carried out using 5 mL of ether. Then, the resultant product was charged with pentafluorobenzyl bromide and 0.8% KOH in ethanol solution (50 μL). The solution was then heated for 1 hour at 50 to 55° C. This reaction solution was diluted with 1 mL of purified water, and extracted with 5 mL of ether. The prepared estradiol-3-pentafluorobenzyl ether was dried for 1 hour under reduced pressure, and the resultant product was charged with 200 μL of a 2% 2-fluoro-1-methyl pyridinium-p-toluene sulfonate/dichloromethane solution and 30 μL of a 10% triethylamine/dichloromethane solution. The resultant mixture was left for 1.5 hours at room temperature. The solvent in this reaction solution was removed by distillation under nitrogen gas. The resultant product was then dissolved in 250 μL of methanol, and diluted with 1 mL of purified water to obtain an estradiol-3-pentafluorobenzyl ether 17-O-methyl pyridinium solution. Subsequently, the product was purified in the same manner as in the estradiol assay for the Stratum Corneum, and then measured by LC-MS/MS.

TABLE 1

| Test Subject | Hormone Level in Stratum Corneum (pg/mg protein) | | | Hormone Level in Saliva (pg/ml) | | |
|---|---|---|---|---|---|---|
| | Estradiol | Progesterone | Testosterone | Estradiol | Progesterone | Testosterone |
| A | 3.09 | 29.80 | 14.46 | 0.635 | 23.31 | 8.43 |
| B | 1.79 | 9.80 | 6.04 | 0.415 | 2.98 | 3.09 |
| C | 1.22 | 31.18 | 4.95 | 1.230 | 35.76 | 3.67 |
| D | 2.02 | 1.79 | 5.08 | 0.500 | 5.44 | 6.31 |

From Table 1, it can be seen that the steroid hormone concentration differs between the stratum corneum and saliva. Further, it can also be seen that measuring the concentration in the stratum corneum is effective in analyzing the impact that a steroid hormone has on the state of the skin.

Example 2

(1) Collection of the Stratum Corneum of the Skin and Preparation of Progesterone Assay Sample The stratum corneum of the skin from the cheek region of 4 male test subjects E, F, G, and H, was collected in the same manner as in Example 1 on PPS tape, and a progesterone assay sample was prepared based on Example 1.

More specifically, $^{13}C_3$-progesterone (100 pg) as a surrogate substance was added at the same time as adding the cut tape into ethanol (27 mL), and then the resultant mixture was shaken for 2 hours at 50° C. The ethanol phase was extracted, and the ethanol was removed by distillation. The obtained extract was dissolved in 250 µL of methanol, then diluted with 1 mL of purified water, and loaded into a pre-washed Bond Elut C18 cartridge column. The resultant product was successively washed with purified water (1 mL) and a 30% acetonitrile aqueous solution (4 mL). Then, the estradiol was eluted with a 40% acetonitrile aqueous solution (3 mL), the progesterone was eluted with a 70% acetonitrile aqueous solution (2 mL), and the solvent in the progesterone eluate was removed by distillation.

A solution of 2% ethylhydroxyammonium chloride (ethoxyamine hydrochloride) in 80% acetonitrile (100 µL) was charged into the obtained progesterone. The resultant mixture was left to react for 18 hours at room temperature, whereby an ethoxyamine derivative formed by imination of the progesterone was produced. Purified water (1 mL) was charged into the reaction solution, extraction with hexane (3 mL) was carried out, and then the solvent was removed by distillation.

Next, the ethoxyamine derivative of progesterone was dissolved in a 70% acetonitrile aqueous solution (100 µL) to obtain an LC-MS/MS sample.

(2) Progesterone Assay

LC-MS/MS measurement was carried out on the above-described LC-MS/MS sample prepared in (1) under the following conditions.

1) LC Conditions
Column: YMC-Pack Pro C18 RS (5 µm, 150×2 mm, YMC, Kyoto)
Column temperature: 40° C.
Mobile phase (solvent): Mixed solution of 10 mM ammonium formate:methanol (1:20)
Rate: 0.2 mL/min 2) MS/MS Conditions
Apparatus: Applied Biosystems API 4000
Ion mode: ESI-MS positive ions
Measurement ion: Progesterone (m/z), 497.5/348
  $13C_3$-Progesterone (m/z), 500.4/351.2

Here, in the progesterone assay, a calibration curve was used in which progesterone (solvent: purified water) labeled with deuterium was used as the internal standard.

The results are shown in Table 2. The values in the table represent the level of progesterone collected by the five strips of PPS tape.

TABLE 2

| Test Subject | Progesterone Level in Stratum Corneum (pg) |
|---|---|
| E | 3.77 |
| F | 4.75 |
| G | 5.24 |
| H | 6.78 |

In the blank test, the two-test average was 0.58 pg. In the test using five strips of PPS tape which had not been adhered to the skin as samples (zero test), the five-test average was 1.76 pg.

From the results of Table 2, it can be seen that the level of progesterone in the stratum corneum of the skin can be assayed.

INDUSTRIAL APPLICABILITY

The steroid hormone assay method according to the present invention is useful in researching the relationship between the state of the skin and the level of estrogen and other hormones in the skin. This steroid hormone assay method is also useful in research and development of cosmetics and beauty treatments based on such relationship.

What is claimed is:

1. A method for assaying the level of a steroid hormone in the body that is in the skin, the method comprising collecting stratum corneum of the skin by a tape stripping method, preparing an assay sample for said steroid hormone from the collected stratum corneum and performing quantitative analysis by LC-MS of the steroid hormone in said sample.

2. The assaying method according to claim 1, wherein the steroid hormone is one or more selected from the group consisting of estrogen, progesterone and testosterone.

3. The assaying method according to claim 1, comprising: extracting estrogen using a solvent from the skin stratum corneum collected by the tape stripping method; introducing a pentahalogenated benzyl group or a pentahalogenated benzoyl group, and a 1-lower alkyl pyridinium group into the extracted estrogen; and then performing the quantitative analysis of the estrogen by LC-MS/MS.

4. The assaying method according to claim 1, comprising: extracting progesterone using a solvent from the skin stratum corneum collected by the tape stripping method; introducing an imino group into the extracted progesterone; and then performing the quantitative analysis of progesterone by LC-MS/MS.

5. The assaying method according to claim 2, wherein the steroid hormone is estrogen.

6. The assaying method according to claim 2, wherein the steroid hormone is progesterone.

7. The assaying method according to claim 2, wherein the steroid hormone is testosterone.

* * * * *